(12) United States Patent
Slone

(10) Patent No.: US 8,226,412 B1
(45) Date of Patent: Jul. 24, 2012

(54) MATRIX WEDGE RESTORATIVE DENTAL APPARATUS AND METHOD OF USE

(76) Inventor: Charles E. Slone, San Juan Capistrano, CA (US)

( * ) Notice: Subject to any disclaimer, the term of this patent is extended or adjusted under 35 U.S.C. 154(b) by 36 days.

(21) Appl. No.: 12/684,437

(22) Filed: Jan. 8, 2010

(51) Int. Cl.
*A61C 5/04* (2006.01)
*A61C 5/00* (2006.01)

(52) U.S. Cl. .......................... 433/215; 433/39; 433/149

(58) Field of Classification Search .................... 433/39, 433/136–138, 4, 80, 148, 149, 153–155, 433/157, 159; 132/232; 81/57.17, 342–348, 81/385, 484
See application file for complete search history.

(56) References Cited

U.S. PATENT DOCUMENTS

| | | | |
|---|---|---|---|
| 351,065 A | 10/1886 | Miller | |
| 782,503 A | 2/1905 | Thompson | |
| 4,259,070 A * | 3/1981 | Soelberg et al. | 433/149 |
| 4,704,087 A | 11/1987 | Dragan | |
| 4,715,816 A | 12/1987 | Mogelof | |
| 5,060,681 A * | 10/1991 | Westbrook et al. | 132/325 |
| 5,197,498 A * | 3/1993 | Stewart | 132/325 |
| 5,573,400 A | 11/1996 | Asher | |
| 6,435,874 B1 | 8/2002 | Hughes | |
| 6,439,886 B1 | 8/2002 | Thoreson | |

* cited by examiner

*Primary Examiner* — Cris L Rodriguez
*Assistant Examiner* — Matthew Seward
(74) *Attorney, Agent, or Firm* — Gene Scott; Patent Law & Venture Group

(57) ABSTRACT

A hand tool engages a pair of opposing matrix wedges that are able to mutually nest when pressed into an interproximal space between adjacent teeth. The hand tool draws a floss tightly thereby causing the wedges mounted on it to move convergently. The wedge elements support a thin matrix band which takes the necessary shape to secure a class II dental preparation.

7 Claims, 11 Drawing Sheets

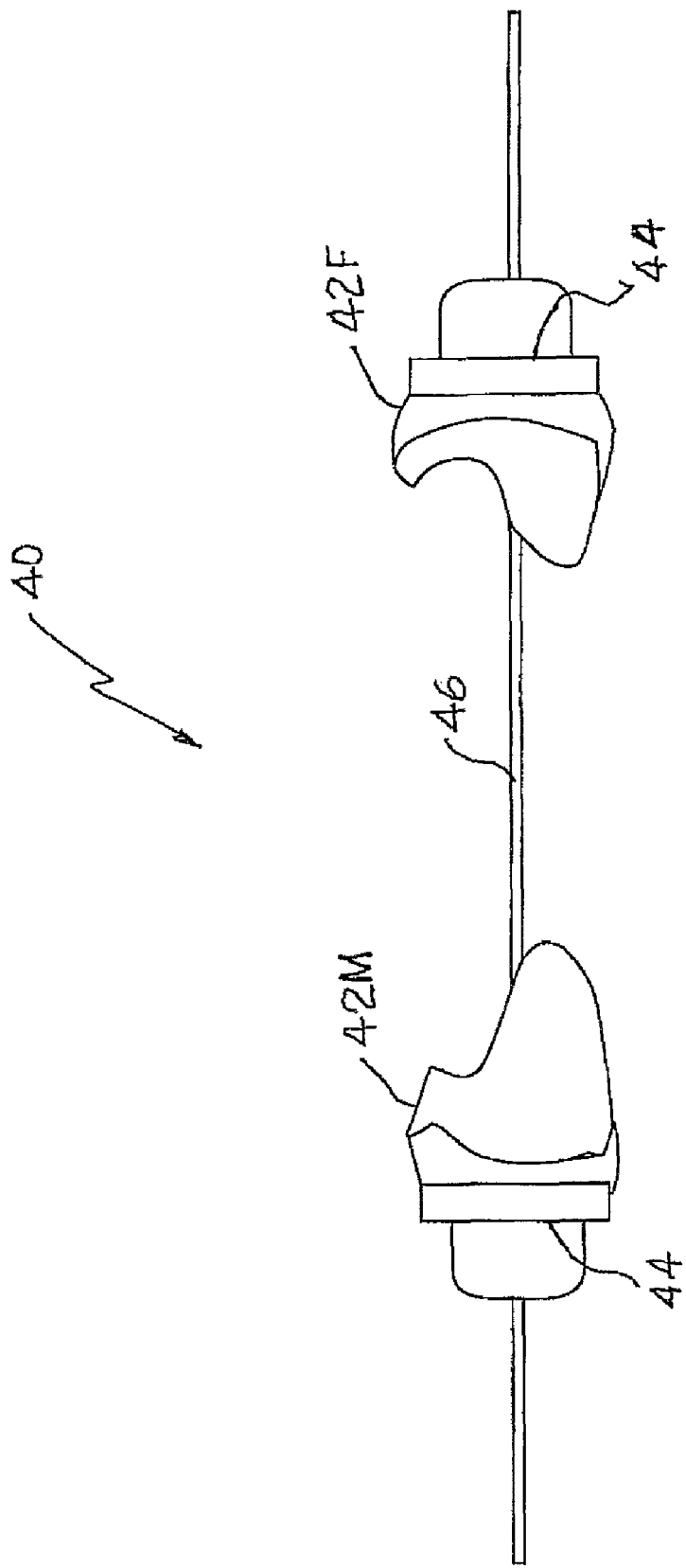

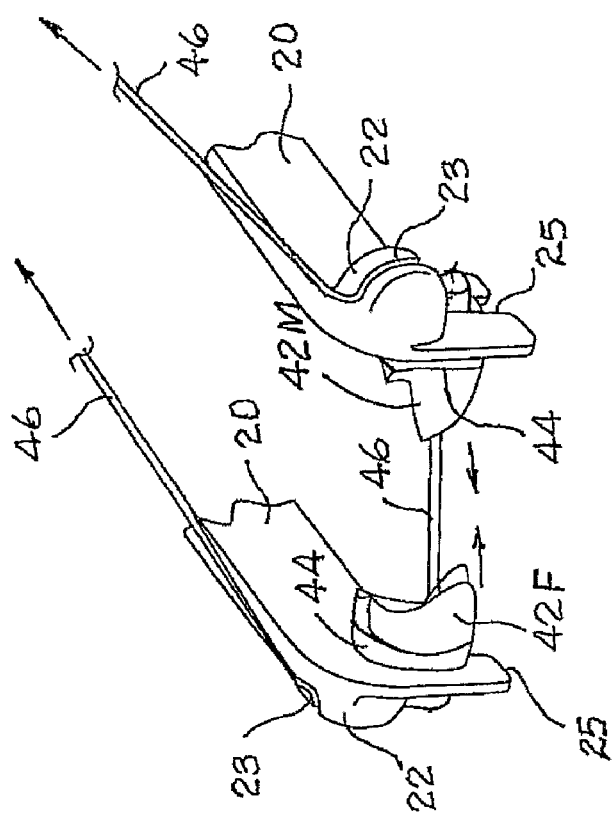
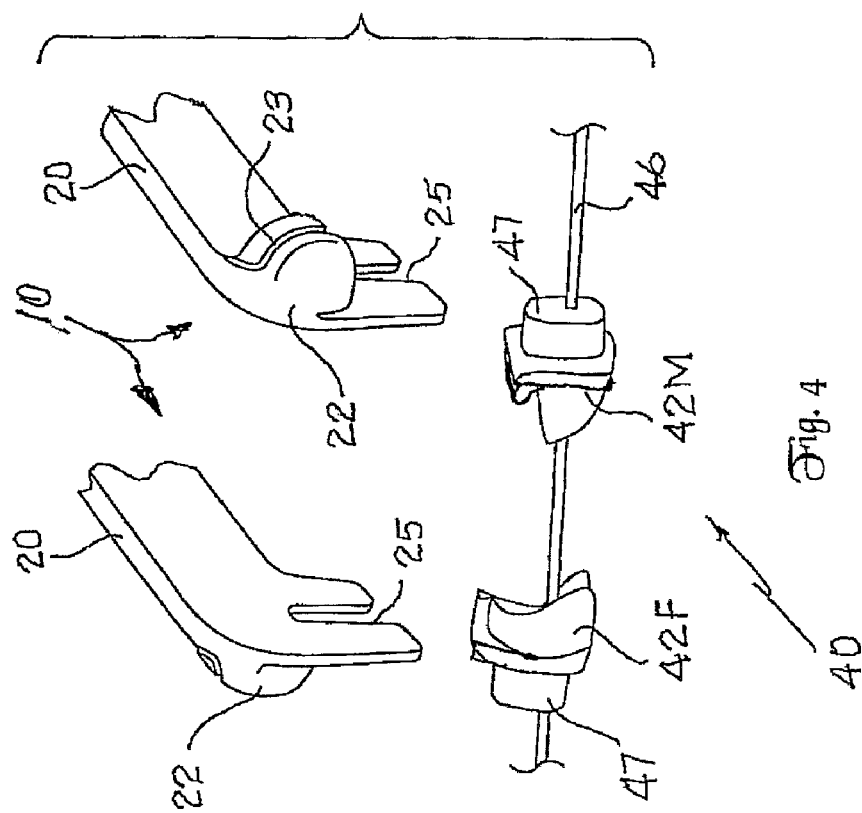

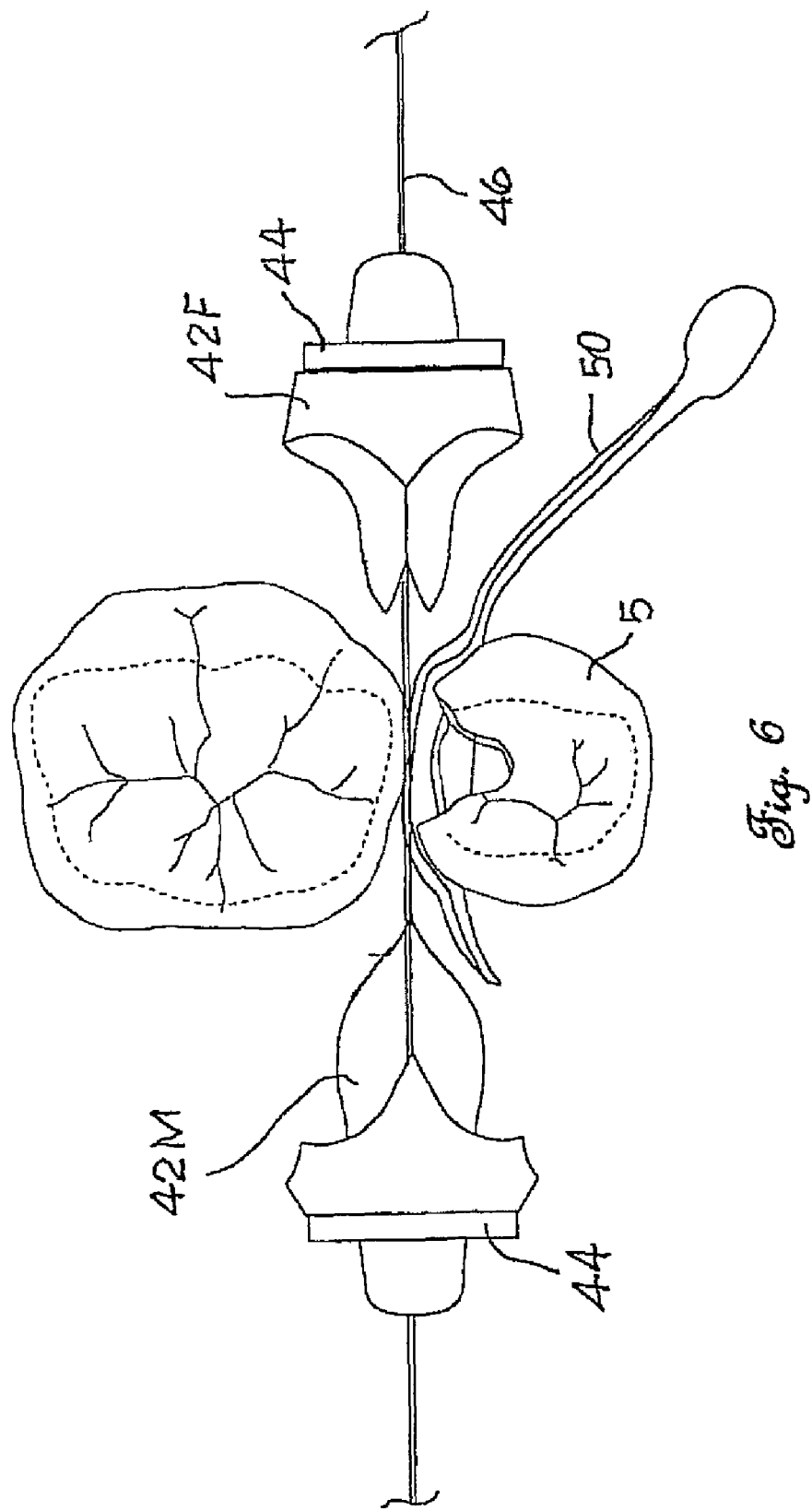

MATRIX WEDGE RESTORATIVE DENTAL APPARATUS AND METHOD OF USE

BACKGROUND OF THE INVENTION

1. Field of the Present Disclosure

The invention described herein relates generally to dental tools and more particularly to a hand tool and its method of use for facilitating a class II dental restoration.

Dental restorations that involve the damaged or lost outer surfaces of a tooth where that surface faces an interproximal space are known as class II restorations. Such restorations present unique problems as the outer surface of the damaged tooth must be returned to its former shape and the mutual contact between the restored tooth and its interproximal neighbor must be returned to its former condition. The standard technique to restore class II tooth surfaces is to surround the missing tooth structure with a temporary form or matrix strip. A matrix strip is usually a thin flexible metal or plastic strip which is inserted between teeth and wrapped around the damaged tooth, the strip being held in place by an adjustable metal retaining clamp. Restorative material, usually composite or amalgam, is then flowed or packed into the space confined by the matrix strip and the remaining tooth structure and then hardened. The shape of the matrix containing the restorative material thus directly defines the resulting exterior contour of the finished restoration. This contour is extremely important to the physiologic health of the tooth and its surrounding hard and soft tissues. If proper contact or contour with the adjacent tooth is not established, food impactions can occur causing periodontal disease or decay. If there is an excess of composite material present around the restoration due to a poorly adapted or positioned matrix, excessive finishing time is required to properly shape the restoration. It is therefore desirable to have a matrix system that replicates the original contour of the tooth as closely as possible, or even improve on it. Such a system must permit restoration in as little time as possible in order to make the procedure cost effective and practical. Also the procedure should be easy for the dentist to learn and to use.

The well known and most commonly used matrix system (Tofflemeyer) comprises three parts: a matrix strip, a matrix strip retainer, and a wedge. The free ends of the matrix strip are connected to the matrix strip retainer, which is placed around the tooth being restored. The matrix strip retainer is then tightened which takes up any slack in the strip and tightens it against the tooth. The shape of the tooth, however, may be quite irregular when the relatively flat matrix strip is tightened against a curved tooth contour that has a missing gap. Also, the thickness of the strip creates an undesirable interproximal space.

Clearly an extremely thin matrix strip that assumes the approximate shape of the original contour of the tooth is desirable. However, it is difficult to insert an extremely thin strip between teeth without tearing or distorting the strip. Wedges are used such as a tapered piece of wood or plastic having a triangular cross section. These are inserted between the teeth and abutting the matrix strip so as to wedge the matrix strip against the lower margins of the restoration between the teeth. This results in an improved anatomical shape in the restoration.

There have been improvements on the standard matrix strip and retainer system such as the Palodent System developed by Dr. Alvin Meyer. This system utilizes an open metal ring with bent ends called a "BiTine Ring," and forms the matrix retainer, serving also as a tooth separator. This system uses a concave shaped sectional matrix along with a conventionally shaped wedge. The technique squeezes the embrasure space, that is, the contour of the surfaces between two teeth, and creates a separating force between the two teeth adjacent to the restoration. The sectional matrix is used with its spherical shape. Its ends are not attached to a matrix retainer, rather the BiTine Rings have bent ends which pinch the matrix against the tooth wall and separate the tooth at the same time. This system creates a better shaped restoration than the flat matrix strip of the Tofflemeyer system, however it has some shortcomings. First, the sectional matrix is spherical or convex, however the lower margin of the restoration (gingival margin) has a flat or even concave topography. Second, since the sectional matrix has no free ends for attachment to a retainer, the matrix cannot be pulled tightly or held tightly against the tooth. The only tightly held areas of the matrix are the small areas of the split ring's contact. This looseness of the matrix results in excess composite at the margins of the restoration causing additional finishing work. Third, the sectional matrix is also made from stamped metal which tens to crinkle and dent as it is being inserted and placed between teeth. Fourth, the split rings can slip off the tooth at an inappropriate time causing delay, extra work and possible damage to the restoration. Fifth, this system utilizes metal matrices which, not being transparent, tends to prevent illumination of a curing light from penetrating into the restoration.

Improved matrix strips are pre-contoured providing better shaped restorations. However, in use, the contoured portion of these strips is difficult to maintain when tightening the strip around the tooth. Also, they are usually a compromising shape that is ill-fitted for other than average sized teeth. Also, in those areas where the strip does not adapt to the tooth, excess composite collects resulting in, as previously stated, more work and time in finishing the restoration.

A matrix system that is adaptable to most tooth contours and all sizes of teeth, which is easy to use, and provides an improved patient experience in not known at this time.

2. Description of Related Art Including Information Disclosed under 37 CFR 1.97 and 1.98

Miller, U.S. Pat. No. 351,065, discloses a dental matrix consisting of two arms or portions fitted for insertion between the tooth to be filled and the adjacent tooth.

Thompson, U.S. Pat. No. 782,503, discloses a dental aid for preventing the packing of fillings into the interproximal spaces between teeth comprising an elongated, deformable, wedge-shaped strip tapering to a point at one end and being triangular in cross-section for insertion between the teeth for pressing a matrix band into conformance with the wall of a tooth at the gingival area of the tooth, the strip being mounted on a strip of dental floss.

Soelberg et al., U.S. Pat. No. 4,259,070, discloses a dental wedge system that has two interfitting circular-bodied wedges adapted to extend between adjacent teeth and to abut and hold a matrix disposed around one of the teeth.

Dragan, U.S. Pat. No. 4,704,087, discloses a retainerless dental matrix band which is preformed or contoured and which can be readily retained in place without a retaining tool. The matrix band comprises a curvilinear base portion having a connected upwardly and outwardly curved portion adapted to complement the shape of a tool and arranged to be disposed within the interproximal space between adjacent teeth, and fixedly retained in place by wedges and/or by bonded cotton pellets. The matrix is constructed for use with self cured or light cured composite resin dental material, and may be made of a light permeable material when used with light-cured composite materials.

Mogelof, U.S. Pat. No. 4,715,816, discloses a dental wedging system that includes an adjustable wedge characterized by a central bore positioned along a longitudinal axis of the wedge. A pair of opposed leaves separate along an apex of the wedge. A piston is used to variably separate the leaves. The adjustable dental wedging system can be used in conjunction with composite dental fibers for ensuring adequate inter-tooth separation.

Asher, U.S. Pat. No. 5,573,400, discloses an expanding dental wedge structure to be used in association with dental matrix bands as used for placing dental restorative materials. The pre-expansion shape in cross section is roughly triangular with the dimensions of the triangle decreasing along the length ending in a pointed manner. The wedge is to be inserted into the area between teeth, one of which is carrying a matrix band. After insertion, the wedge is exposed to moisture causing pronounced expansion, which through equal pressure on the tooth surfaces and gingival tissues involved does: press the matrix tightly against the tooth sealing out moisture contamination, absorb moisture, drying the surgical field, and decreases blood flow and subsequent bacterial and vital transmission.

Hughes, U.S. Pat. No. 6,435,874, discloses structures and methods which may be used for applying force to the base of a matrix band or cavity filling material mold during a cavity filling procedure. In a preferred exemplary embodiment of the present invention, a unitary body of elastic material is stretched preferably by applying force in opposite directions to the opposite ends of the unitary body such that a central portion of the body of material is thinned. The thinned portion of the unitary body may then be easily inserted in the space between two adjacent teeth next to the base of a matrix band or cavity filling material mold. After the unitary body has been inserted into the space between two adjacent teeth next to the base of the matrix band or cavity filling material mold, the force which has been applied to the opposite ends of the unitary body is then removed. As a result, the previously stretched elastic unitary body contracts and becomes thicker in its central portion that had been previously thinned. The contraction and thickening of the unitary body in the space between adjacent teeth fills this space and applies and outward force to the walls of this cavity. Accordingly, the contracted unitary body applies a force on the base of the matrix band or cavity filling material mold which forces the base of the matrix band or filling material mold adjacent to the base of the tooth to be filled.

Thoreson, U.S. Pat. No. 6,439,886, discloses a device having pliable walls for placement in the mouth of a patent to serve, in one manner, as a matrix barrier with walls of the device bearing upon opposed tooth surfaces. An inlet permits inflation of the device, as by a dental syringe, of the installed device. A valve closes under air pressure to seal the inlet which may also be closed by a fused inlet segment.

The related art described above discloses a very wide range of matrix systems. This indicates that there is a strong interest and need for improvements in this technology. The present disclosure distinguishes over the prior art providing heretofore unknown and significant advantages as described in the following summary.

BRIEF SUMMARY OF THE INVENTION

The present detailed description teaches a matrix wedge restorative dental apparatus that uses a hand tool to move matrix wedge elements into place between adjacent teeth. The wedge elements are mounted on spaced apart ends of a flexible arch of the tool and are joined by a length of cord, which is set between the adjacent teeth. The cord extends laterally from the wedges and is drawn to a slide mounted on the tool so that when the slide is pulled along the tool in a direction away from the wedges, the arch's ends are forced to converge thereby pushing the wedges into the interproximal space between the teeth from opposing sides to form an effective restoration boundry. The cord is engaged frictionally within the wedges so that it tends to hold the wedges in place during restoration.

A primary objective inherent in the above described apparatus and method of use is to provide advantages not taught by the prior art.

Another objective is to provide an apparatus and method for more easily forming supporting a matrix strip in a class II restoration.

A further objective is to produce an improved contact in a class II restoration.

A still further objective is to reduce the amount of clean-up necessary after a class II restoration.

A still further objective is to provide a means for supporting a matrix band that is adaptable to most tooth contours and all sizes of teeth.

A still further objective is to provide an easy to use matrix band placement in a class II restoration.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWINGS

Illustrated in the accompanying drawings is at least one of the best mode embodiments of the present invention In such drawings:

FIG. 3 is a side elevational view of a matrix wedge assembly of the invention;

FIG. 4 is a partial perspective view showing a forward end of the hand tool positioned above the matrix wedge assembly in preparation for engagement therewith;

FIG. 5 is a partial perspective view showing the forward end of the hand tool engaged with the matrix wedge assembly and with ends of a length of cord, part of the matrix wedge assembly, conducted within grooves in the hand tool;

FIG. 6 is a plan view showing the matrix wedge assembly and a matrix strip engaged with an interproximal space in preparation for a class II restoration;

DETAILED DESCRIPTION OF THE INVENTION

The above described drawing figures illustrate the described apparatus and its method of use in at least one of its preferred, best mode embodiment, which is further defined in detail in the following description. Those having ordinary skill in the art may be able to make alterations and modifications what is described herein without departing from its spirit and scope. Therefore, it must be understood that what is illustrated is set forth only for the purposes of example and that it should not be taken as a limitation in the scope of the present apparatus and method of use.

Figure 1:
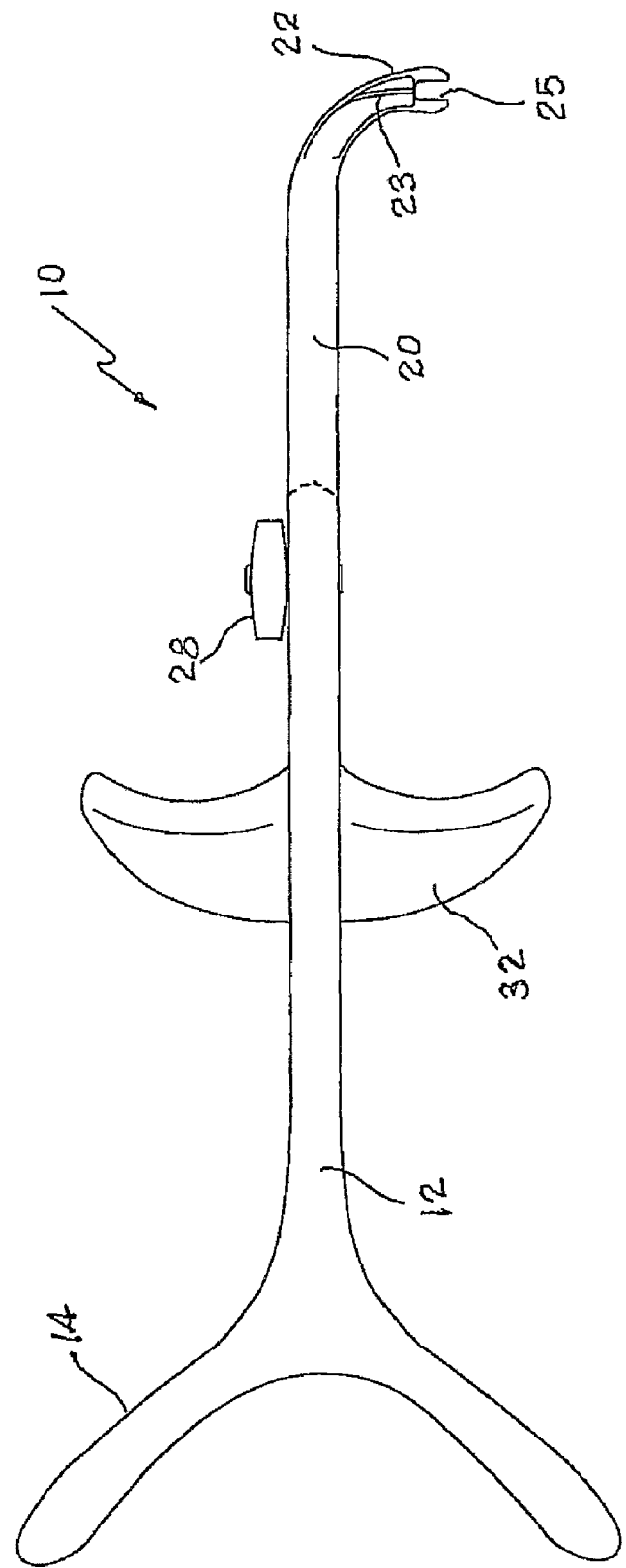
FIG. 1 is a side elevational view of a hand tool of the present invention.
Figure 2:
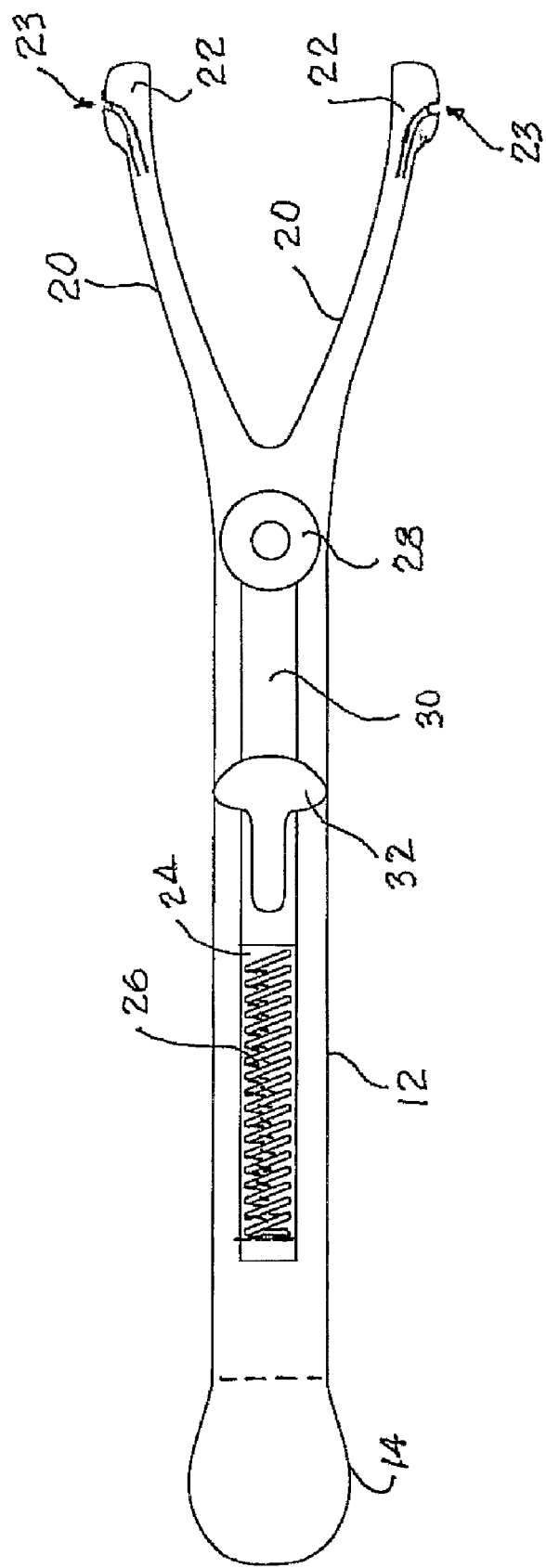
FIG. 2 is a top plan view thereof.
Figure 7:
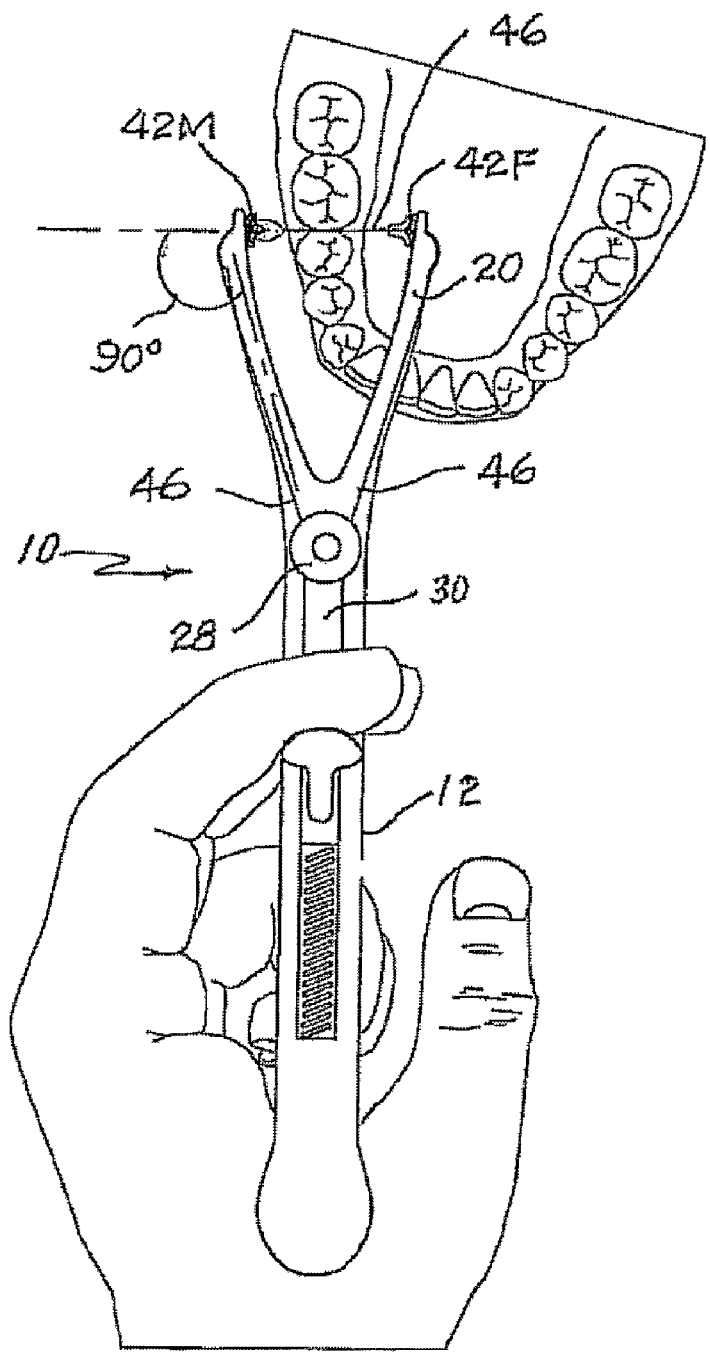
FIG. 7 is similar to FIG. 6 showing the hand tool engaged with the matrix wedge assembly; for improved clarity, the matrix strip is not shown.
Figure 12:
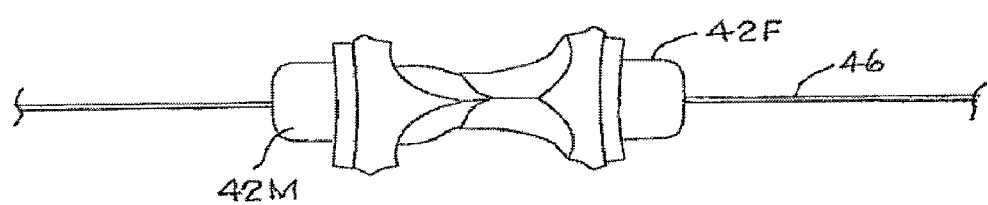
FIG. 12 is a top plan view of the matrix wedges as fully mutually engaged as in FIG. 11.

The present invention is a dental hand tool 10 (FIGS. 1 and 2), that is used with a replaceable matrix wedge assembly 40 (FIGS. 4, 6, 11-13), which is a part of the present invention, and also with a matrix strip 50 (FIGS. 6 and 12), which is not a part of the present invention. As shown in FIGS. 1 and 2, the tool 10 comprises an elongate shaft 12 with a hand rest 14 extensive rearwardly on the shaft 12, and a pair of spaced apart flexible arms 20 extensive forwardly of the shaft 12. Each of the flexible arms 20 terminates with a gripper element 22 presenting a slot 25 as is best shown in FIG. 4. Gripper element 22 may be as shown, or otherwise, as any alternative element that is able to grip, from above, a matrix wedge 42 of matrix wedge assembly 40, as is shown in FIGS. 4 and 5. A slider 30 is engaged medially in a groove 24 of the shaft 12, and is movable between forward (FIGS. 7, 9 and 10) and rearward (FIG. 8) positions on the shaft 12 as illustrated. A finger grip 32 enables one hand held against rest 14 to pull the slider 30 rearward. Preferably, a spring 26 is positioned in the shaft groove 24 so as to urge the slider 30 forwardly when hand pressure is relaxed. The slider 30 preferably includes a tie-off wheel 28 for tying off portions of a length of floss, as will be explained.

The matrix wedge assembly 40, as shown in side elevation in FIG. 3, and from above in FIG. 6, comprises a pair of matrix wedges which shall be references generically by numeral 42, a male wedge 42M, and a female wedge 42F, and both are spaced apart and mounted on a length of cord 46. The term "cord" as used herein has the meaning of a flexible fine floss or filament made of natural or manufactured fibers such as polyester or other materials, and may be commercial dental floss or other types of such highly flexible thread or thread-like materials having relatively high tensile strength. The wedges 42 are made of a flexible and compliant rubber or plastic and are shaped so that the male wedge 42M is able to enter the female wedge 42F and thereby laterally force the expansion of the female wedge 42. It should be noticed that the cord 46 is extensive through the bodies of the wedges 42 (FIG. 4) and extends laterally beyond the wedges 42 to the left and to the right. In this disclosure we refer to the length of cord 46 that lies between the wedges 42 as the medial portion of the length of cord 46, and the two free end portions of the length of cord 46 as those portions extending laterally away from the wedges 42. The wedges 42 are secured to the length of cord 46 in such manner that they may be slid along the length of cord 46, but only by applying an axial force. Those of skill will know how to mold the wedges 42 around the length of cord 46 so as to attain a desired level of sliding friction. As shown in FIGS. 4 and 5, the grippers 25 are forced over and around the wedges 42 and positioned up against flanges 44.

As can be seen in FIG. 2, each of the flexible arms 20 provides a guiding groove 23 for the length of cord 46, so that, as shown in FIG. 5, the lateral portions of length of cord 46 are engaged within the guiding grooves 23 and therefrom they are extended and clamped in tie-off wheel 28. It should be noticed also that the guiding grooves 23 are so curved as to turn the lateral portions of length of cord 46 by at least 90° with respect to the medial portion of the length of cord 46.

Figure 8:
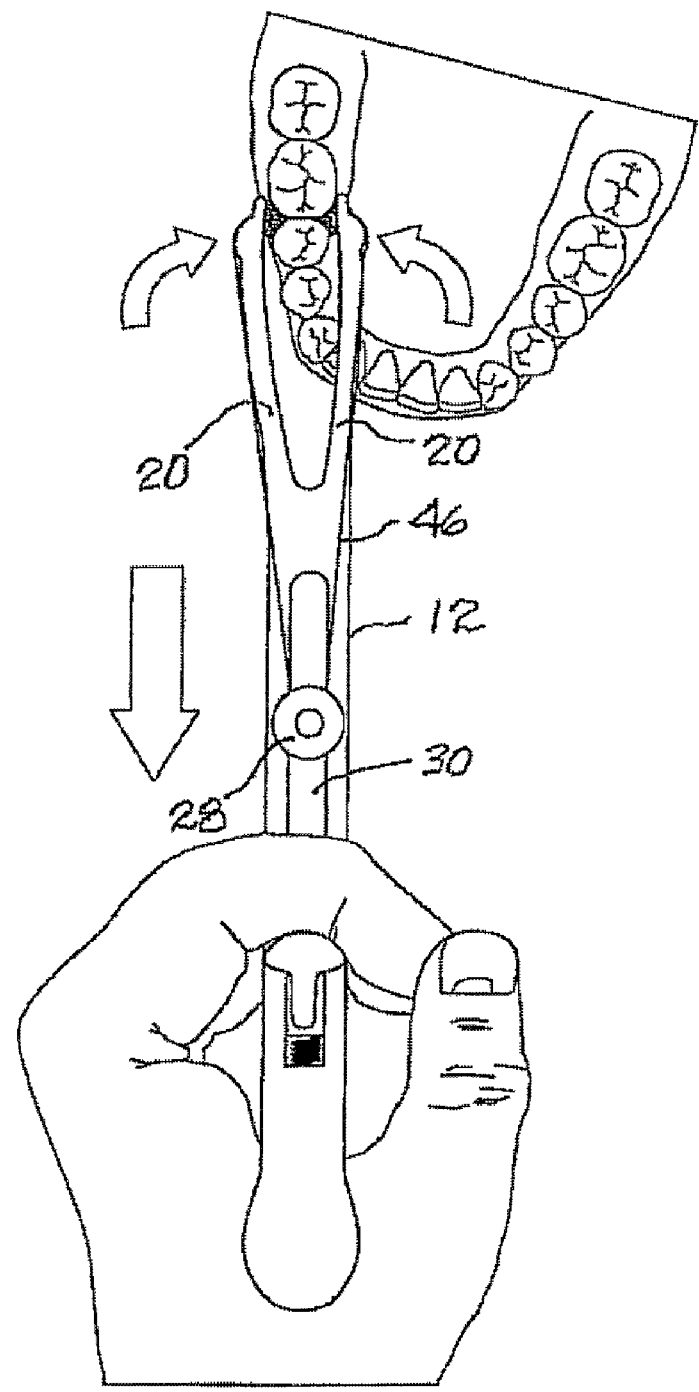
FIG. 8 is similar to FIG. 7 demonstrating how the hand tool achieves insertion of the matrix wedges fully into the interproximal space.
Figure 13:
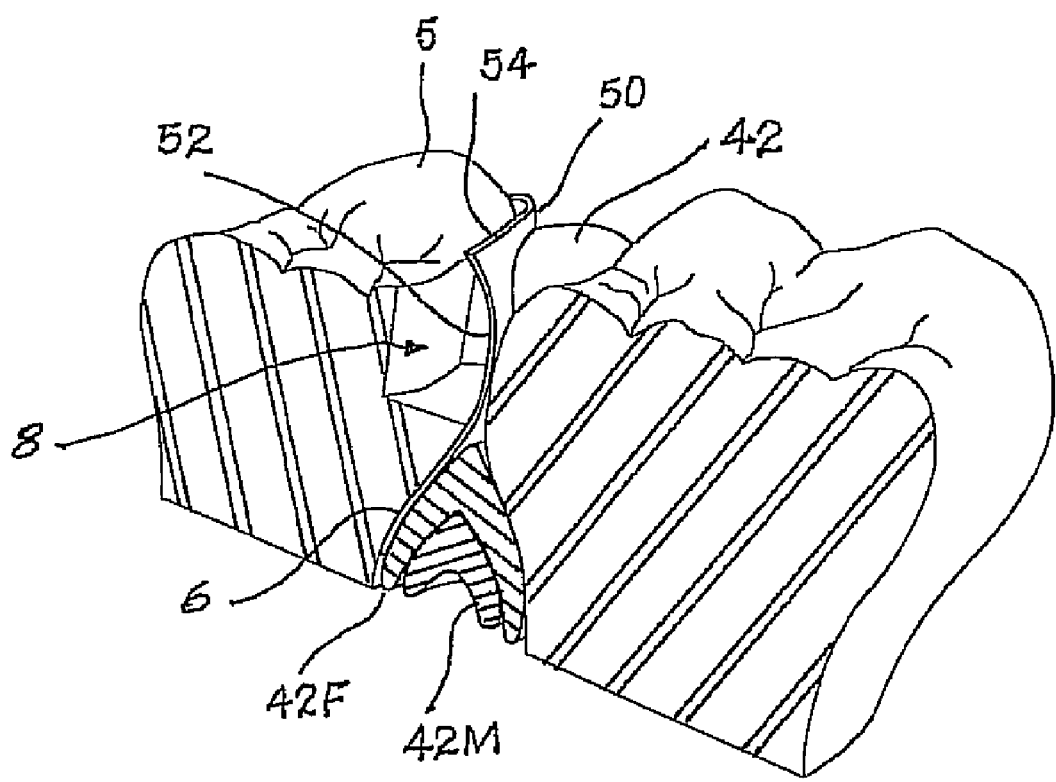
FIG. 13 is a perspective vertical cross section taken along line 13-13 in FIG. 11 showing the two adjacent teeth, a portion of the matrix strip and portions of the matrix wedges demonstrating how the matrix wedges force the matrix strip into a desired shape against the target tooth.

The present invention is used for establishing a strong contact between the matrix strip 50 and a tooth that has been prepared for a class II restoration, the "prepared tooth 5," and, for creating a restraining surface 52 of the matrix strip 50 that is spaced apart from but adjacent to the prepared tooth 5. Before describing the method of the present invention, we refer to FIG. 13. In this figure we see the finished results of the present method. The matrix strip 50 ideally conforms to a lower concave surface 6 of the prepared tooth 5, but also conforms to an upper convex portion of the prepared tooth 5 which includes missing portions 8 of the prepared tooth, that is, those portions that have been damaged and removed prior to reconstruction of the prepared tooth and the missing upper convex portion. Because the matrix strip 50 is highly flexible with relatively little stiffness of its own, it needs to be supported and pressed against the outside surface of the prepared tooth 5 while enabling the restoration to be formed as close to the adjacent tooth as possible, and preferably making contact therewith. FIG. 13 shows how this is accomplished with the present invention. The female wedge 42F receives the male portion 42M and is therefore expanded by the male portion 42M as they nest. This causes the female portion 43 is press against the outer surface of the lower portion of the matrix strip 50, pressing it against the lower surface of tooth 5, and this prevents restoration material (not shown) from forcing its way into the interproximal space. At the same time the upper portions of both of the wedges 42 press against the exterior upper surface of the matrix strip 50 supporting it in place and causing it to slightly roll over along the top edge 54. Such a confirmation of the matrix strip is ideal in forming a restoration that has an outer surface as close to the adjacent tooth as possible and in replicating the original tooth configuration. In most instances, good contact is achieved between the restored tooth 5 and its adjacent tooth. The procedure includes the steps of engaging the matrix strip 50 between the adjacent teeth (FIG. 6) into the interproximal space, mounting the pair of matrix wedges 42 in spaced apart positions on the length of cord 46 (FIGS. 3-6), engaging the gripper elements 22 of the hand tool 10 with the matrix wedges 42 (FIGS. 4 and 5), engaging lateral portions of the length of cord 46 with the floss guiding grooves 23 (FIG. 5), and then with the slider 30 (FIG. 7) of the hand tool 10, inserting the medial portion of the length of cord 46 between the adjacent teeth (FIGS. 6 and 7), and finally, drawing the slider 30 away from the adjacent teeth thereby forcing the gripper elements 22 and matrix wedges 42 into convergence and mutual engagement of the matrix wedges 42 within and interproximal space (FIGS. 8 and 13), thereby supporting the matrix strip 50 in readiness for placement of the restoration material which will fill the prepared cavity and abut surface 52 of the matrix strip 50. In FIG. 8 arrows show the movement of the slide 30 rearward on the shaft 10 and also show the coordinated movement of the wedges 42 as they are pushed into place.

Figure 9:
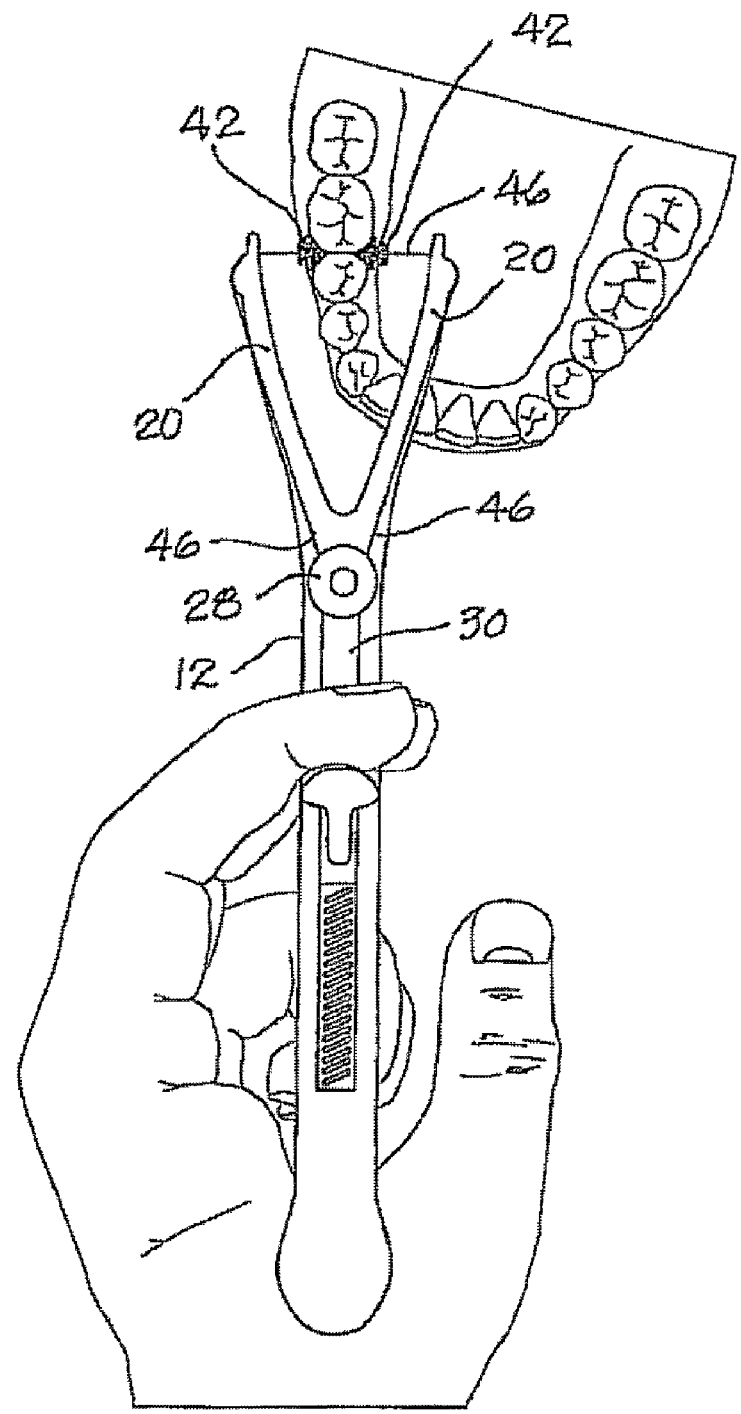
FIG. 9 is similar to FIG. 8 demonstrating disengagement of the hand tool from the matrix wedges.
Figure 10:
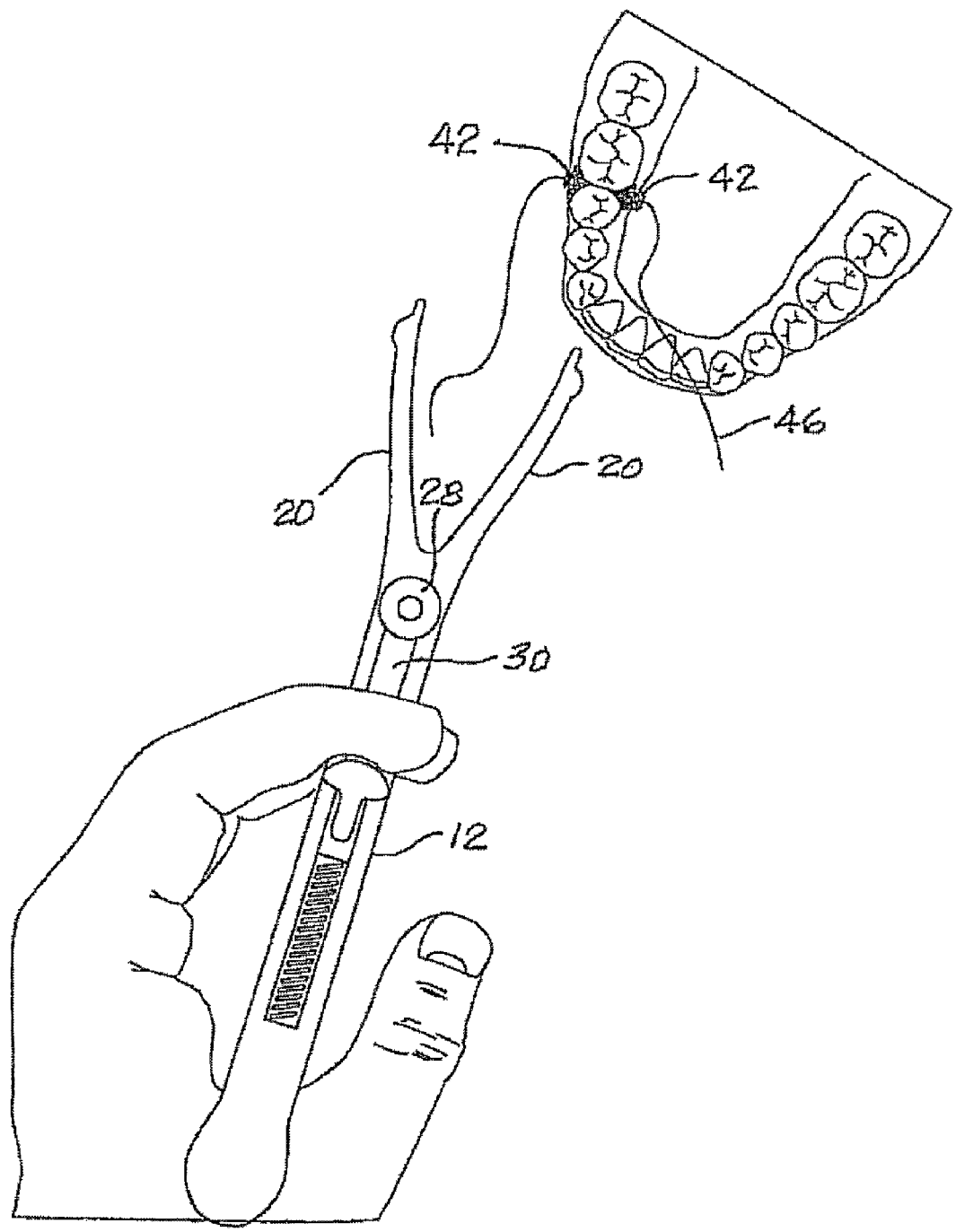
FIG. 10 is similar to FIG. 9 demonstrating disengagement of the hand tool from the cord.
Figure 11:
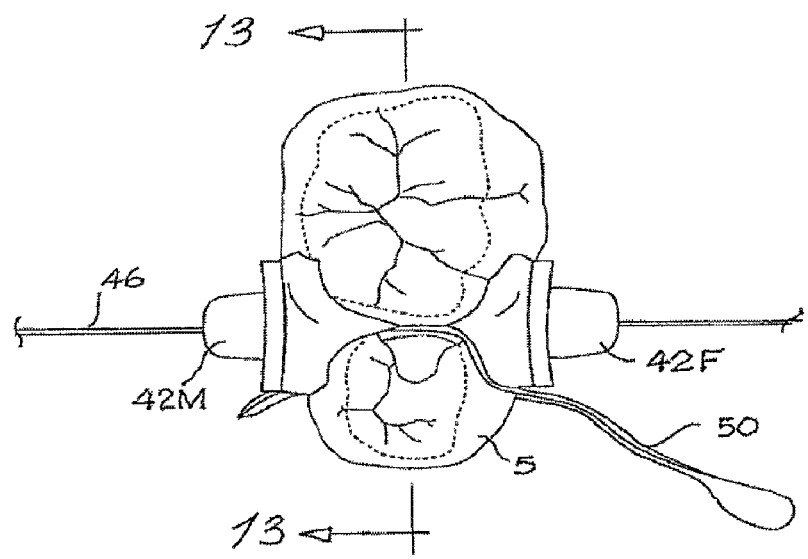
FIG. 11 is an enlarged view of the teeth of FIG. 10 and additionally showing the matrix strip in place as in FIG. 6, and showing the matrix wedges fully inserted.

FIG. 9 shows the hand tool 10 as separated from the wedges 42 after their placement into the interproximal space, and with spring tension released. FIG. 10 shows the length of cord 46 released from the hand tool 10 whereupon the hand tool 10 is removed and the restoration process is started. Once the wedges 42 have been placed, they are elastically held in place by compressive forces exerted by the adjacent teeth and also because the portions of the wedges 42 shown in section in FIG. 13 act to clamp each other in place.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A dental hand tool for use with a matrix strip for establishing a strong contact between the matrix strip and a tooth with a class II restoration preparation, and, for creating a restraining surface adjacent to the tooth, the hand tool comprising:
    an elongate shaft having a pair of spaced apart flexible arms extensive forwardly on the shaft, each of the flexible arms terminating with a gripper element;
    a slider slidingly engaged with the shaft and movable between forward and rearward positions thereon;
    a matrix wedge assembly comprising a pair of matrix wedges, each matrix wedge removably engaged with one said gripper element, the matrix wedges joined by a length of cord;
    opposing lateral portions of the length of cord engaged with the slider wherein
    drawing the slider rearwardly on the elongate shaft moves the gripper elements
    and matrix wedges toward mutual abuttment;
    whereby, the matrix wedges, when mutually engaged within an interproximal space, press the matrix strip into a desired conformation against the tooth creating the restraining surface enabling the class II reconstruction of the tooth.

2. The dental hand tool of claim 1 wherein the matrix wedges are formed and shaped so as to mutually nest.

3. The dental hand tool of claim 1 wherein the flexible arms have guiding grooves, the lateral portions of the length of cord engaged slidingly within the guiding grooves and terminated in a tie-off wheel secured to the slider.

4. The dental hand tool of claim 3 wherein the guiding grooves are curved in a manner directing the lateral portions to a means for tieing-off.

5. The dental hand tool of claim 1 further comprising a spring secured by the shaft, the spring adapted and positioned to urge the slider forwardly along the shaft when the slider is not restrained manually.

6. A method of applying a dental hand tool for establishing a strong contact between a matrix strip and a tooth with a class II restoration preparation, and, for creating a restraining surface adjacent to the tooth; the method comprising the steps of:
    inserting a matrix strip into an interproximal space adjacent to the preparation;
    mounting a pair of matrix wedges in spaced apart positions on a length of cord;
    engaging gripper elements of flexible arms of the hand tool with the matrix wedges;
    engaging opposing lateral portions of the length of cord with a slider of the hand tool;
    inserting a medial portion of the length of cord into the interproximal space;
    drawing the slider away from the tooth thereby forcing the flexible arms, gripper elements, and the matrix wedges into convergence and mutual engagement of the matrix wedges within the interproximal space, thereby forcing the matrix strip into contact with the tooth, and forming a preferred contour of the matrix strip thereby defining the restraining surface.

7. The method of claim 6, further comprising the step of inserting the opposing lateral portions of the length of cord into guiding grooves on the flexible arms of the hand tool, the guiding grooves directing the length of cord to a tie-off wheel on the slider.

* * * * *